United States Patent
Rainey

[11] Patent Number: 5,975,896
[45] Date of Patent: Nov. 2, 1999

[54] NON-ROTARY CARIES REMOVAL AND RESTORATION SYSTEM

[76] Inventor: J. Tim Rainey, P.O. Box 1044, Refugio, Tex. 78377

[21] Appl. No.: 09/187,157

[22] Filed: Nov. 6, 1998

Related U.S. Application Data

[60] Provisional application No. 60/066,985, Nov. 28, 1998.

[51] Int. Cl.$^6$ ............................................. A61C 1/07
[52] U.S. Cl. .............................. 433/86; 433/82; 604/82
[58] Field of Search .............................. 433/80, 82, 84, 433/86, 119; 604/82, 83

[56] References Cited

U.S. PATENT DOCUMENTS

| | | | |
|---|---|---|---|
| 3,718,973 | 3/1973 | Slater et al. | 433/84 |
| 3,924,335 | 12/1975 | Balamuth et al. | 433/119 |
| 4,276,023 | 6/1981 | Phillips et al. | 433/82 |
| 4,770,632 | 9/1988 | Ruder et al. | 433/80 |
| 5,087,198 | 2/1992 | Castellini | 433/80 |
| 5,171,301 | 12/1992 | Vanderveen | 604/83 |
| 5,199,604 | 4/1993 | Palmer et al. | 433/80 |
| 5,295,829 | 3/1994 | Frey et al. | 433/82 |
| 5,419,703 | 5/1995 | Warrin et al. | 433/86 |
| 5,762,495 | 6/1998 | Pinel et al. | 433/84 |
| 5,853,290 | 12/1998 | Winston | 433/86 |

*Primary Examiner*—Ralph A. Lewis
*Attorney, Agent, or Firm*—Royston, Rayzor, Vickery, Novak & Druce, L.L.P.

[57] ABSTRACT

A non-rotary caries removal and restoration system for use in the treatment of tooth structures. The system includes at least two solution constituent reservoirs adapted to separately store the constituents of a solution capable of abating organic tooth decay. Each of the solution constituent reservoirs are fluidly connected to an activation reservoir by means of pump and solution constituent conduits. The activation reservoir is adapted to receive, mix, and activate the solution constituents to form and hold said solution. A solution channel is fluidly connected to the activation reservoir by a solution conduit and adapted to dispense the solution upon or into a carious lesion having an organic component or matrix of decay. A handpiece shaped for hand use houses driver adapted to communicate sonic energy to an energy transfer tip. The energy transfer tip is releaseably coupled to the driver and configured to agitate the solution dispensed upon or into the carious lesion or matrix of tooth decay. A selectively engageable driver activation device is connected to the driver allowing an operator to selectively engage the driver to agitate the solution dispensed upon or into the carious lesion or matrix of tooth decay.

6 Claims, 1 Drawing Sheet

NON-ROTARY CARIES REMOVAL AND RESTORATION SYSTEM

RELATED PATENT APPLICATIONS

This patent application claims priority to U.S. Provisional Application Ser. No. 60/066,985 filed Nov. 28, 1998 entitled NON-ROTARY CARIES REMOVAL AND RESTORATION SYSTEM, which application in its entirety is hereby expressly incorporated by reference into the present application.

DESCRIPTION

1. Technical Field

The present invention relates generally to the dental field, and more specifically to the removal of the organic decay component of a carious lesion and restoration of the healthy tooth structure.

2. Background Art

Various methods are employed in modern dentistry to remediate and restore a decaying tooth structure. The most common present-day method of restoration includes the mechanical drilling and removal of the decaying area and a portion of the healthy tooth structure thereabout. This procedure is invasive in that it cuts into the healthy tooth structure and therefore has the potential for causing the patient pain and resultingly requires anesthesia. Previously, it has also been discovered that a solution of N-monochloro-DL-2-aminobutyrate, commonly referred to as NAMB, is useful in the abatement of the organic component of tooth decay.

In previous procedures, the NAMB solution is applied to the decaying area, but must be massaged or agitated manually against the carious lesion. As a result, such a procedure was only usable upon flat and easily accessible tooth structures. In practice, this accounted for about 5% of all carious lesions. In view of the fact that very few situations of decay could be treated using NAMB, and the fact that such treatment was labor intensive and time consuming, such procedures have never enjoyed popularity and have for all practical purposes disappeared from practice.

In view of the above described deficiencies associated with the method of dentistry to remediate and restore a decaying tooth, the present invention has been developed to alleviate these drawbacks and provide further benefits to the user. These enhancements and benefits are described in greater detail hereinbelow with respect to several alternative embodiments of the present invention.

DISCLOSURE OF THE INVENTION

The present invention in its several disclosed embodiments alleviates the drawbacks described above with respect to previously known employments of NAMB as a caries removal procedure and incorporates several additionally beneficial features.

It has been discovered that the ability of the NAMB solution to remove the organic component of decay in a carious lesion is significantly enhanced and potentiated when exposed to sonic and ultrasonic energy. Still further, through the use of sonic and ultrasonic agitation of the NAMB solution within a carious lesion, the organic component of the decay can be dislodged and removed therefrom substantially more quickly than previous techniques realized. Through the use of a microscopic energy transfer tip for imparting such agitating sonic energy to the solution, almost all lesions are accessible; not just those lesions on substantially flat tooth surfaces. By using a common hand piece that carries the sonic energy transfer tip and dispenses the NAMB solution, utilization and application of this invention for caries removal and restoration is facilitated. Still further, the energy transfer tips may be selected so that during the agitation stage of the NAMB solution, the tip does not engage the tooth structure and therefore there is no invasion into the tooth structure which can cause pain requiring anesthesia. If appropriately chosen, however, the energy transfer tip may then be engaged upon the tooth surface for cutting healthy tooth structure in further preparation for subsequent restoration procedures.

The general beneficial effects described above apply generally to each of the exemplary descriptions and characterizations of the devices and mechanisms disclosed herein. The specific structures through which these benefits are delivered will be described in detail hereinbelow.

BRIEF DESCRIPTION OF THE DRAWINGS

The invention will now be described in greater detail in the following way of example only and with reference to the attached drawings, in which.

MODE(S) FOR CARRYING OUT THE INVENTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a basis for the claims and as a representative basis for teaching one skilled in the art to variously employ the present invention.

Furthermore, elements may be recited as being "coupled"; this terminology's use contemplates elements being connected together in such a way that there may be other components interstitially located between the specified elements, and that the elements so specified may be connected in fixed or movable relation one to the other. Certain components may be described as being "adjacent" to one another. In these instances, it is expected that a relationship so characterized shall be interpreted to mean that the components are located proximate to one another, but not necessarily in contact with each other. Normally there will be an absence of other components positioned therebetween, but this is not a requirement. Still further, some structural relationships or orientations may be designated with the word "substantially". In those cases, it is meant that the relationship or orientation is as described, with allowances for variations that do not effect the cooperation of the so described component or components.

Figure 1:
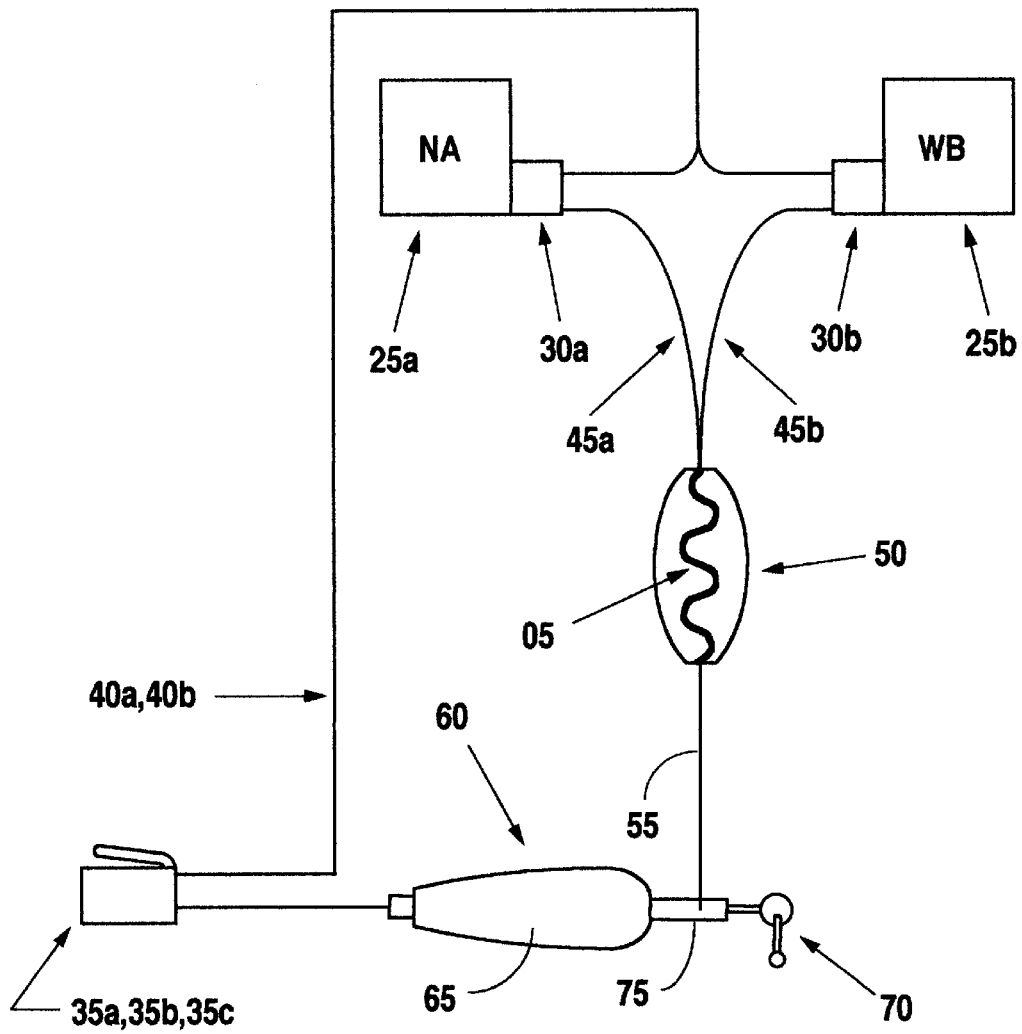
FIG. 1 is a schematic illustration of the several components of the non-rotary caries removal and restoration system.
Figure 2:
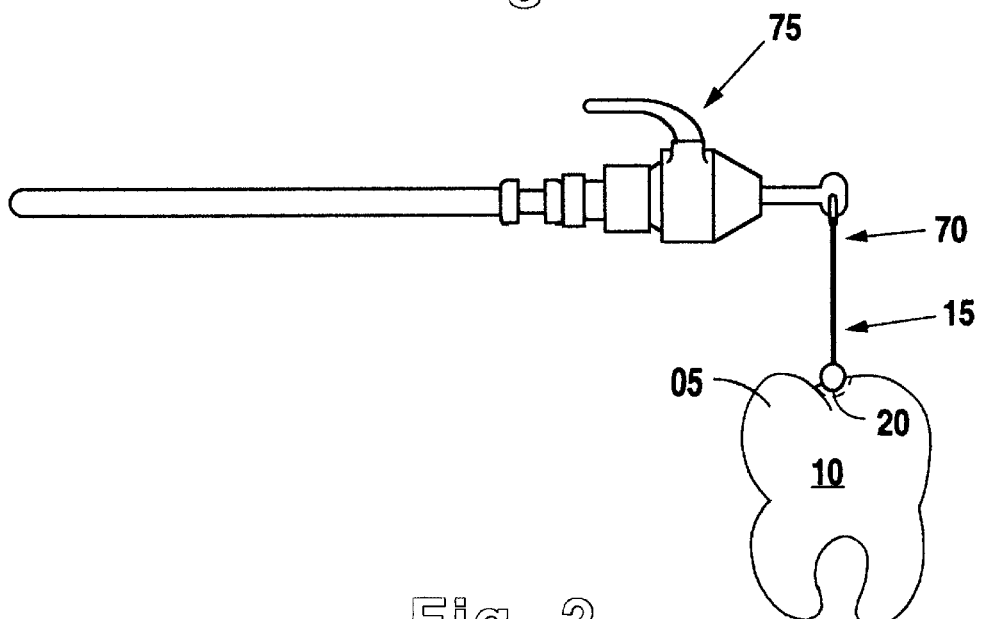
FIG. 2 is a more detailed illustration of a hand piece and its administration upon a carious lesion.

Referring to FIG. 1, a hand piece 60 may be seen to which N-monochloro-DL-2-aminobutyrate (NAMB solution) 05 is supplied. The NAMB solution is delivered from a mixing or activation reservoir 50 wherein the two inactive NA and MB components of the solution are mixed and activated. Each component of the solution 05 is stored separately in a NA reservoir 25a and a MB reservoir 25b. Each reservoir has a pump 30a,30b associated therewith that is engaged using an activation foot pedal 35a,35b that is selectively engageable by an operator. The depressed versus non-depressed status of the pedal 35 is typically transferred via a communicator 40a,40b normally taking the form of a wired connection. From each reservoir 25, conduits 45a and 45b connect each respective reservoir to the mixing reservoir 50. Within the reservoir 50, the NAMB is mixed together and chemically activated. It is then conveyed through a NAMB conduit 55 to the hand piece 60 for dispensing upon or into a carious lesion 15 having an organic component or matrix of decay 20. The decay component is almost always surrounded by healthy mineralized tooth structure 10 that is intact and to be restored and preserved.

It has been discovered that not only is NAMB chemically activated when mixed together, but its efficacy is potentiated when exposed to sonic and/or ultrasonic energy. Therefore, the hand piece 60 through which the NAMB solution is dispensed includes a sonic or ultrasonic driver 65 whose sonic energy or power is communicated to an energy transfer tip 70. Like the pumping of the constituent components of the NAMB solution, and the solution 05 itself, the sonic driver 65 is activated using a foot pedal 35c that is depressible by the operator. In use, the NAMB solution is dispensed through a conveyance or channel 75 in the hand piece 60 adjacent and proximate to the energy transfer tip 70. In this manner, the NAMB solution is dispensed upon the carious lesion 15 and excited by the sonic energy of the transfer tip 70. The transfer tip 70 may take any one of several selectable forms that include bur shanks roughened with carbide, diamond burs, or even endodontic sonic and ultrasonic files. Because the surfaces of these several transfer tips are not smooth, their movement in response to the sonic driver 65 causes agitation and circulation of the NAMB solution upon the carious lesion. Responsively, the organic component of the decay 20 is chemically affected by the sonically enhanced NAMB solution and physically agitated and removed by the energy transfer tip 70. Because these tips 70 may be quite small, previously impossible to reach locations upon tooth structures are accessible to the present invention, even if magnification is required for the viewing the procedure.

After the decaying matter has been removed using the NAMB solution in a relatively quick procedure, the same transfer tip 70, if appropriately selected, can be used to cut and/or abrade the remaining mineralized tooth structure 10 in further preparation for subsequent restorative procedures. It is in this cutting capacity, that sonically and ultrasonically driven burs, shanks, and files have been previously utilized.

Although the present invention has been described and illustrated in detail, it is to be clearly understood that the same is by way of illustration and example only, and is not to be taken as a limitation. The spirit and scope of the present invention are to be limited only by the terms of any claims that may be presented hereafter.

INDUSTRIAL APPLICABILITY

The present invention finds applicability in the dental fields, and more specifically in the removal of organic decay from carious lesions and the restorative procedure of the remaining mineralized tooth structure.

What is claimed and desired to be secured by Letters Patent is as follows:

1. A non-rotary caries removal and restoration system for use in the treatment of tooth structures, said system comprising:

at least two solution constituent reservoirs adapted to separately store constituents of a solution capable of abating organic tooth decay;

a plurality of solution constituent reservoir pumps, one each of said pumps being fluidly connected to each of said solution constituent reservoirs for pumping said solution constituents from each of said solution constituent reservoirs;

a plurality of selectively engageable pump actuators, one each of said actuators being connected to each of said solution constituent reservoir pumps allowing each of said solution constituent reservoir pumps to operate independently;

an activation reservoir fluidly connected to each of said solution constituent reservoir pumps by solution constituent conduits, said activation reservoir adapted to receive, mix, activate and retain activated solution;

a solution channel fluidly connected to said activation reservoir by an activated solution conduit, said solution channel adapted to dispense activated solution upon carious tooth structure;

a handpiece configured to house a driver and shaped for hand use;

a driver coupled to said housing, said driver adapted to communicate sonic energy;

an energy transfer tip releaseably coupled to said driver to receive said sonic energy communicated by said driver, said energy transfer tip adapted for agitation of said activated solution that has been dispensed upon carious tooth structure; and a selectively engageable actuator connected to said driver allowing an operator to selectively engage said driver and agitate said activated solution on said carious tooth structure.

2. A non-rotary caries removal and restoration system as retained in claim 1, wherein said solution channel is positioned and fixed adjacent to said energy transfer tip enabling an operator to use a single hand to dispense and agitate said activated solution.

3. A non-rotary caries removal and restoration system as recited in claim 1, wherein said activated solution is N-monochloro-DL-2-aminoburyrate (NAMB) comprised of the constitutents NA and MB.

4. A non-rotary caries removal and restoration system as recited in claim 1, wherein each of said selectively engageable pump actuators are controlled by foot pedals.

5. A non-rotary caries removal and restoration system as recited in claim 1, wherein said energy transfer tip can be selected from the group of bur shanks roughened with carbide, diamond burs, endodontic sonic files, and ultrasonic files.

6. A non-rotary caries removal and restoration system as recited in claim 1, wherein said energy transfer tip is adapted to cut and abrade tooth structure and can be selected from the group of sonically driven burs, shanks and files.

* * * * *